US010926077B2

(12) United States Patent
Pagano, II et al.

(10) Patent No.: US 10,926,077 B2
(45) Date of Patent: Feb. 23, 2021

(54) INTERCHANGEABLE LOCKABLE CATHETER

(71) Applicants: Nunzio P. Pagano, II, Asheville, NC (US); Peter L. Pagano, Raleigh, NC (US)

(72) Inventors: Nunzio P. Pagano, II, Asheville, NC (US); Peter L. Pagano, Raleigh, NC (US); Curtis W. Thornton, Pittsboro, NC (US)

(73) Assignees: Nunzio P. Pagano, II, Asheville, NC (US); Peter L. Pagano, Raleigh, NC (US)

( * ) Notice: Subject to any disclaimer, the term of this patent is extended or adjusted under 35 U.S.C. 154(b) by 29 days.

(21) Appl. No.: 15/593,012

(22) Filed: May 11, 2017

(65) Prior Publication Data
US 2017/0326349 A1    Nov. 16, 2017

Related U.S. Application Data

(60) Provisional application No. 62/334,482, filed on May 11, 2016.

(51) Int. Cl.
*A61M 39/10*    (2006.01)
*A61M 39/20*    (2006.01)
(Continued)

(52) U.S. Cl.
CPC ...... *A61M 39/105* (2013.01); *A61M 39/1011* (2013.01); *A61M 39/20* (2013.01);
(Continued)

(58) Field of Classification Search
CPC ............ A61M 39/105; A61M 25/0097; A61M 39/1011; A61M 39/22; A61M 39/10;
(Continued)

(56) References Cited

U.S. PATENT DOCUMENTS 557,423 A * 3/1896 Outhouse ............ F16L 37/0841
285/317
4,701,159 A * 10/1987 Brown ................ A61M 5/1582
604/175
(Continued)

FOREIGN PATENT DOCUMENTS

WO        2015123689 A1    8/2015
WO   WO 2015123689 A1 *  8/2015 ........ A61M 25/0097

OTHER PUBLICATIONS

PCT Search Report and Written Opinion from Corresponding Application No. PCT/US2017/032236.
(Continued)

*Primary Examiner* — Nathan R Price
*Assistant Examiner* — Melissa A Snyder
(74) *Attorney, Agent, or Firm* — NK Patent Law

(57) ABSTRACT

The present invention relates to a novel interchangeable lockable catheter having a cap, the cap locking onto a junction hub or base, and encasing at least one lumen proximally to the junction hub of a multi-lumen catheter, PICC line and the like. The interchangeable lockable catheter's cap and base may be made of more than one piece, and provide a locking mechanism sufficient to deter tampering, while providing a low profile, comfortable, sanitary, and efficient means of closing off lumens for patients leaving the treatment area.

7 Claims, 14 Drawing Sheets

(51) Int. Cl.
*A61M 39/22* (2006.01)
*A61M 25/02* (2006.01)
*A61M 25/00* (2006.01)

(52) U.S. Cl.
CPC ......... *A61M 39/22* (2013.01); *A61M 25/0097* (2013.01); *A61M 2025/0286* (2013.01); *A61M 2039/1027* (2013.01); *A61M 2039/1033* (2013.01); *A61M 2039/1072* (2013.01); *A61M 2039/1077* (2013.01)

(58) Field of Classification Search
CPC ...... A61M 25/0014; A61M 2025/0007; A61M 25/0026; A61M 2025/0036; A61M 2039/1027; A61M 2039/1077; F16L 37/08; F16L 37/0841; F16L 37/086
See application file for complete search history.

(56) References Cited

U.S. PATENT DOCUMENTS

| | | | |
|---|---|---|---|
| 4,804,208 A * | 2/1989 | Dye | F16L 37/56 285/124.4 |
| 7,901,396 B2 | 3/2011 | Shah et al. | |
| 2003/0088213 A1 | 5/2003 | Schweikert et al. | |
| 2005/0055012 A1 | 3/2005 | Trerotola | |
| 2005/0256461 A1 | 11/2005 | DiFiore et al. | |
| 2005/0267445 A1* | 12/2005 | Mendels | A61M 39/10 604/534 |
| 2008/0214991 A1 | 9/2008 | Haarala et al. | |
| 2009/0224529 A1* | 9/2009 | Gill | A61M 39/10 285/23 |
| 2013/0204206 A1 | 8/2013 | Morgan et al. | |
| 2017/0043126 A1* | 2/2017 | Jones | A61M 25/0097 |

OTHER PUBLICATIONS

Bayer Materialscience, LLC. "Snap-Fit Joints for Plastics—A Design Guide." pp. 2-26. Bayer Polycarbonates Business Unit. Pittsburgh, Pennsylvania.

* cited by examiner

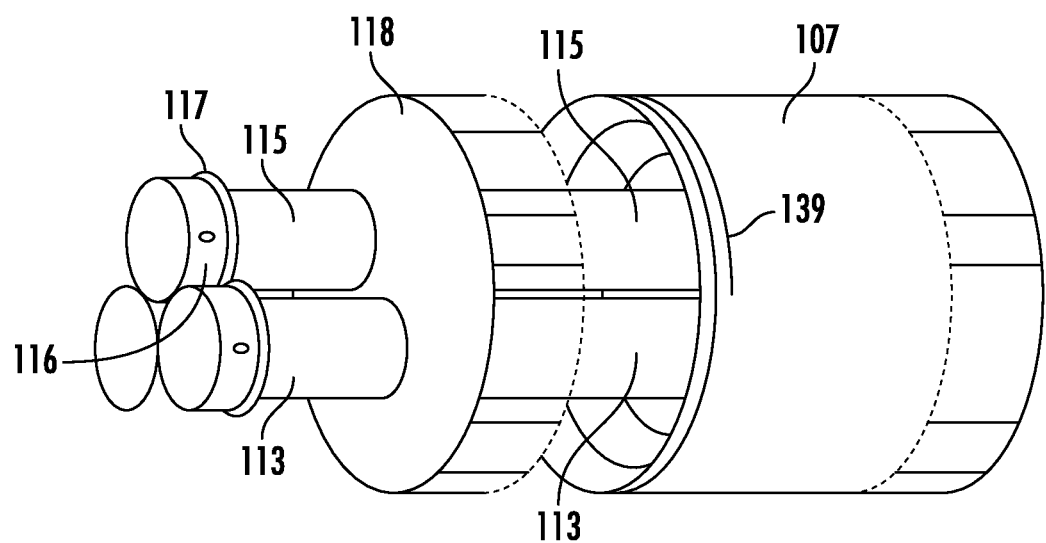
FIG. 3
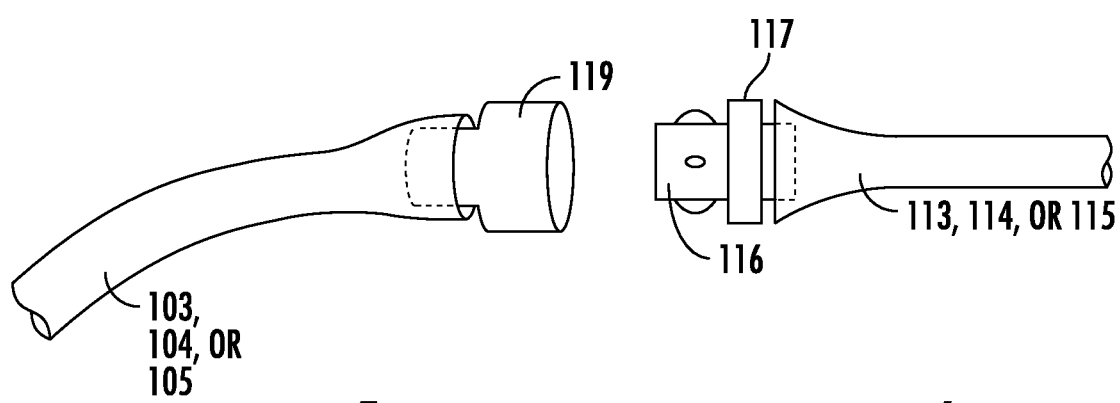
FIG. 5  FIG. 4

INTERCHANGEABLE LOCKABLE CATHETER

This application claims priority to a U.S. provisional application No. 62/334,482 filed on May 11, 2016 and which is incorporated herein in its entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

Field of the Invention

The present invention relates to a novel interchangeable venous lockable catheter having a cap, the cap locking onto a junction hub or base, and encasing at least one lumen proximally to the junction hub of a multi-lumen venous catheter, peripherally inserted central catheters (PICC) line and the like. The interchangeable lockable catheter's cap and base may be made of more than one piece and provide a locking mechanism sufficient to deter tampering while providing a low profile, comfortable, sanitary, and efficient means of closing off lumens for patients leaving the treatment area.

Description of Related Art

Intravenous (IV) access is essential in hospital medicine. IV access provides methods for fluid resuscitation, drug administration, and nutritional support in some patients. Peripheral IV access is appropriate for most patients; however, PICC and central venous catheters are needed for long term IV access and infusion of certain medications.

PICCs provide a common means of maintaining IV access in hospitalized patients and are now commonly placed for discharge purposes. The utilization of PICC lines have increased significantly. According to the idata research, the PICC market was valued at $413 million in 2011 and is expected to reach $583 million in 2017. PICC use is expected to increase with the increase in the aging population and in conjunction with Medicare payment bundling which demands shorter length of stay and improved outcomes.

Current PICC line apparatus are fixed one-piece devices. The number of lumens can vary from single to triple lumen for each catheter. The number of lumens is fixed, there is no technology that allows for manipulation of that number by either increasing or decreasing, without exchanging the entire catheter. Where the number of lumens must be changed, the patient is subjected to new catheter placement, increased medical spending, inconvenience, discomfort, and risk of complications.

The complications and limitations with PICC lines are well documented. Infections with traditional PICCs are well known, allowing bacteria to be introduced directly into the bloodstream (known as central line-associated infections (CLABSI)). After infection has taken hold, the incidence of morbidity and mortality are high, and concomitantly, the cost of care where infection has occurred is very high. These infections, as well as thrombotic catheter occlusions, are well-known critical issues in healthcare. Central lines also put patients at risk for thrombosis (forming of blood clots), including both upper and lower extremity deep vein thrombosis. Moreover, venous catheters placed in the chest increase the patient's risk for a pneumothorax. Other complications include misplacement, embolisms, hemorrhage, and venous fusion among many others.

Many advances have been made to combat risk of infection including valves, caps, and antimicrobial and antithromboic devices. Antimicrobial coatings used in the manufacture of PICC lines reduce infection risk, but it cannot eliminate it. Moreover, current venous catheters allow lumens to hang at significant length from the hub junction with a plastic cap for each lumen extending therefrom.

Despite advances in the functionality of the venous catheter, the general structure of the product has not changed. The device is large, bulky, fixed in regards to number of lumens, and accessible to the patient. Currently, the junction hub terminates in the lumen, or multiple lumens. Those lumens hang from the junction hub and are closed off by a cap having at least one piece. These hang from the junction hub as the patient is discharged. Each cap, in one embodiment, measures approximately 1 cm in width and 4.0-4.5 cm in height. When a three-lumen port is prepared, the result is three tubes hanging from the outlet, each with its own cap hanging therefrom. These aspects cause inconvenience and discomfort for the patient, complicate management for the physician which result in unnecessary healthcare expenditures.

Additionally, large and bulky nature of the traditional device has the added disadvantage of supplying a larger surface area. While this obviously complicates the ability to secure the device to the patient, it also increases the probability of contact with harmful bacteria and subsequent catheter associated infections.

The large PICC line device also increases the risk of both intentional and accidental device movement. Decannulation is a common occurrence among patients with impaired cognition (either medically induced or otherwise). The bulky device provides a large target for such patients to remove their catheter entirely. Decannulation has its highest incidence in the morning and evening. This timing, unfortunately, provides a logistic conundrum, in that this coincides with the most difficult time to regain venous access. Thus, decannulation can result in prolonged hospital stay, wasted hospital resources, and cause unnecessary risk for the patient. It may also result in unnecessary and inconvenient short-term venous catheter placement before long-term venous access can be regained.

While posing a particular problem for the impaired patient, the large surface area increases the risk of accidental movement of the catheter by the daily activities of the patient. The dangling lumens with their stops/end caps can impact the patient's activities of daily living (ADLs), at the very least, they are inconvenient. For instance, when bathing, the dangling lumens must be covered and secured, often necessitating a caregiver to assist. Lastly, the large dangling device is tedious for the outpatient to keep for long-term access and is inconvenient for working professionals or those patients attempting to work towards their rehabilitation goals.

A common issue in the inpatient setting is the number of lumens needed for the patient. Patients are commonly discharged with single lumen catheters. The amount of access can change on a daily basis depending on the patient's clinical status. A patient who receives a single lumen PICC, which is commonly placed for hospital discharge, may medically decompensate during the hospital stay or outpatients may require admission into a hospital that may require an increased lumen need if they are not clinically stable. This scenario could result in repeated unnecessary procedures, delay in care, and increases healthcare expenditures. Some have provided systems that allow for a hub with dual lumens (U.S. Pat. No. 7,901,396), or systems allowing for the manipulation of components within the hub (U.S. Patent Application Publication No. 20130204206). Others have created hub systems that are detachable, such as in U.S. Patent Application Publication NO. 20080214991. None of these systems, however, allow for the locking of one or more lumens while allowing access to desired lumens for flushing and the like. Moreover, these systems do not provide a low-profile, compact design for outpatient use, and use with impaired patients.

Accessibility to the venous catheter is a very common clinical conundrum. The recent increase in intravenous drug abuse (IVDA) among the general population has only highlighted and exacerbated the issue. Patients who abuse intravenous drugs through accessing their venous catheter are at an increased risk for complications such as catheter-associated infections and detrimental impacts on outcomes. This unnecessarily results in a large waste of healthcare dollars and places added stress on providers and patients as well as their caregivers. Few documents contemplate a locking mechanism on venous catheters. For instance, U.S. Patent Application Publication No. 20050055012 describes a multi-lumen stoppage device with a locking mechanism. That lock is a leur lock, and locks the lumen separately, does not aggregate the lumens together, or provide any low-profile system.

A common and controversial topic includes the discharge of the patient with a history of IVDA with a placed venous catheter. Easy access to the bloodstream can prove irresistible, resulting in the patient removing the stop to a lumen and inputting non-prescribed/illicit drugs. Access to lumens by the patient carries a significant risk of infection through the central line. Common infections include endocarditis, osteomyelitis, and discitis, treatment of which commonly requires weeks to months of antibiotics. Patients contracting these infections as a result of IVDA commonly are admitted throughout the entirety of their treatment because of their need for continued intravenous access for antibiotic therapy. This is a significant strain on healthcare resources as well as the patient and their loved ones.

Inappropriate patient access of the PICC is not only an issue for patients with venous catheters in their home environment. IVDA is a common occurrence even in the hospitalized patient. Patients are commonly found to be accessing their own venous catheters while admitted into hospital to self-administer non-prescribed/illicit drugs inappropriately. This commonly results in patients being placed in monitored beds which utilizes scarce resources within the hospital and impairs overall performance of hospital staff thus impacting care for other patients.

There is a need for the significant reduction in size of dangling lumen stops and lumens from the traditional multi-lumen venous catheter which is also tamper-proof and significantly inhibits detrimental bacterial colonization. The present apparatus meets such needs and provides further related advantages.

BRIEF SUMMARY OF THE INVENTION

The present invention describes a low profile and low surface area device that caps a/the lumen(s) extending from a catheter (referred to here as an interchangeable lockable catheter, or "ILC"). The device is more convenient for the patient, provides a smaller target for patient for self-removal, and is less cumbersome for continuation of the patient's ADLs upon discharge. The cap of the ILC gives providers the chance to modulate number of lumens based on the patient's clinical status and need. The low profile cap of the ILC decreases accessibility for inappropriate use, decreases rate of infections, decreases length of hospital stay with patients with a history of IVDA, and is less prone to accidental removal. The tamper resistant and tamper evident cap decreases the need for inpatient observation thus freeing resources within staff, decreasing monitored bed use, and improving overall care.

The ILC of the present invention offers a significant financial benefit when used as it includes the catheter itself, the lumen exchange, and the tamper-resistant caps.

In one embodiment, the interchangeable lockable catheter offers a user the ability to up or down regulate the number of lumens at any time based on the patient's current medical need. Changing accessibility to lumens is simple and efficient, being accomplished by a nurse at bedside in a matter of minutes.

In another embodiment, the ILC has a two-piece design. In this embodiment, the ILC includes the catheter itself that is inserted into the vessel in a standard PICC line fashion with the junction hub sutured or secured onto the skin. The base of the ILC has four points of contact, or each side of the device, to ensure good contact and to form a proper seal with a cap.

In yet another embodiment, the four points of contact from the interchangeable portion of the ILC rely on a hooking device and three levers on the base that lock with the cap to provide a tamper-resistant and tamper-evident cap.

In most embodiments, the ILC has a locking, tamper-resistant, and tamper-evident cap.

In one embodiment, interchangeable portion of the ILC houses male inserts based on the number of lumens required.

In another embodiment, the ILC is a tamper resistant/evident cap having a push insert base comprising a pull-tab and breakaway twist cap attachment.

In another embodiment, the ILC is manufactured using a medical grade plastic that is either antiseptic in nature or coated to be antiseptic.

In these embodiments, the ILC is applied after the junction hub and allows for traditional dressing to be untouched (i.e., lumens extend beyond the junction hub before ILC placement).

In an alternate embodiment, the ILC is applied and is in contact with the junction hub.

In one embodiment, the ILC has a tubing carriage capable of attaching lumens to the ILC for access to lumens by a health professional.

In another embodiment, the ILC comprises a female receiving piece for each lumen capable of accepting a male insert with raised knots to form a seal with the female piece and residing within the cap of the ILC.

In another embodiment, the ILC has a plastic binder which secures the male inserts and provides a contact point for a screw cap. Wherein the ILC is substantially flat in nature, as in yet another embodiment, the male inserts are in the cap which has perforated clips for break away, one-time use.

In some embodiments, the screw cap of the ILC has a sliding screw cap which forms a seal with the base. The sliding screw cap, in some embodiments, may allow for at least one lumen to egress from the cap while capping at least one other lumen and those capped lumens may have a capped end within the screw cap that allows for penetration for flushing purposes.

In further embodiments, the base of the ILC has a threaded female accepting base having a plurality of openings adequate to accept at least one lumen and having at least one flange to further secure the screw cap of the ILC.

In yet other embodiments, the ILC can be configured for use with one, two, three, four, or five lumens extending from the junction hub.

These and other aspects of the present invention will become evident upon reference to the following detailed description and attached drawings.

BRIEF DESCRIPTION OF THE DRAWINGS

FIG. 3 is an illustration of the screw cap of the circular ILC, as in one embodiment.

FIG. 4 is an illustration of the male inserts connecting to the extension lumen, as in one embodiment of the ILC.

FIG. 5 is an illustration of the female receiving piece from the lumen, as in one embodiment of the ILC.

DETAILED DESCRIPTION OF THE INVENTION

Figure 1:
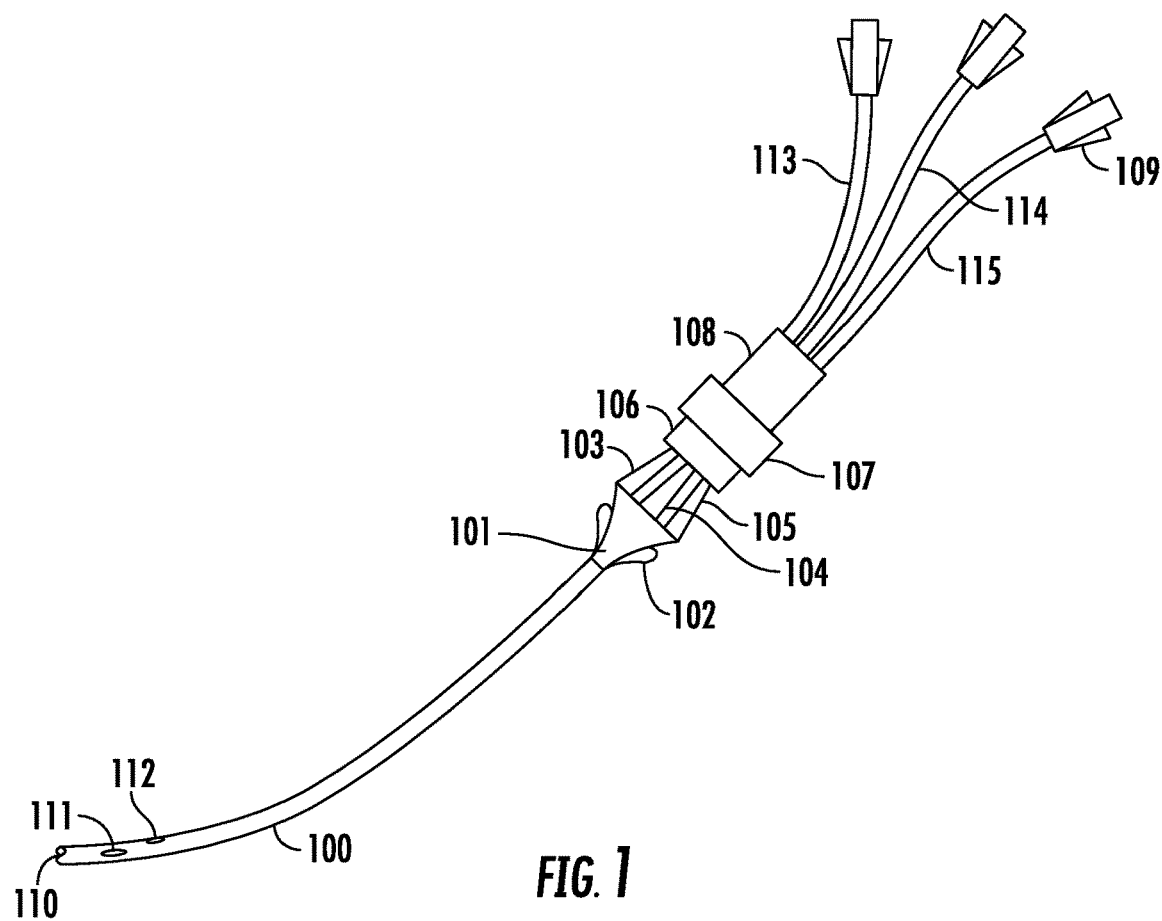
FIG. 1 is an illustration of the ILC with a detachable tubing carriage, as in one embodiment.

Provided herein is a description of multiple configurations of an ILC capable of locking at least one lumen, providing antiseptic support, and, relative to a traditional PICC line, a small, singular extension from the catheter.

Throughout this application, references are made to various embodiments relating to the apparatus and its method of use. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the interchangeable lockable catheter.

In the present description, any concentration range, percentage range, ratio range or other integer range is to be understood to include the value of any integer within the recited range and, when appropriate, fractions thereof (such as one tenth and one hundredth of an integer), unless otherwise indicated. As used herein, "about" or "comprising essentially of" means+/−15%. The use of alternative (i.e., or) should be understood to mean one, both, or any combination thereof of the alternatives. As used herein, the use of an indefinite article, such as "a" or "an," should be understood to refer to the singular and the plural of a noun or noun phrase.

The term "comprising" is not intended to limit inventions to only claiming the present invention with such comprising language. Any invention using the term comprising could be separated into one or more claims using "consisting" or "consisting of" claim language and is so intended.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein the term "interchangeable lockable catheter (ILC)" refers to a PICC line catheter which can attach one or more different tubes by means of interchangeable tubing cartridges having 1 to 190 or more tubes connecting to the single line catheter.

As used herein the term "subject" refers to a patient, normally human, but in one embodiment, the subject is a mammal in need of a single venous catheter for peripheral insertion into a vessel of the subject.

As used herein the term "a single venous catheter for peripheral insertion into a vessel" refers to having a proximal end for insertion into a vessel of the subject as a single venous catheter. The distal end is connected to a junction hub.

As used herein the term "junction hub" refers to a connect device which attaches one or more lumens to the single venous catheter distal end. In one embodiment, it is a plurality of lumens. By attaching a tubing cartridge, one or more tubes can be connected to the single line by replacement of the tubing cartridge.

As used herein the term "base" refers to a device which is removable or attached which is configured to receive the one or more lumens in the junction hub. The lumens will extend through the base to attach to one or more tubes for delivery of liquids to the single venous catheter. The base can be any shape, such as circular, rectangular, or, in one embodiment, essentially flat (rectangular looking).

As used herein the term "tubing cartridge" refers to a device which attaches to the base for attaching the one or more tubing to the one or more lumens in the system thus allowing multiple sources to be fed to the single line catheter. The tubing cartridge can attach by any means but in one embodiment it attaches with a pin and spring mechanism as shown in the figures.

As used herein the term "cap" refers to a device for attaching to the base to seal the base when a tubing cartridge is not attached. The cap can be screwed or snapped on or by any means. as desired. In one embodiment, it is constructed to be tamper resistant, as shown in the drawings, or otherwise. The cap can also be fitted with a penatratable layer such that tubing can be inserted through the penatratable layer.

Throughout the description of the ILC, materials to manufacture the device are described as "medical grade plastics." Medical grade plastics include polymers with capability of sterilization, long-term durability, low leaching and extractability, and long shelf life and aging. Medical grade plastics include polymers either alone or in combination of, but not limited to: polyethylene, polypropylene, polystyrene, polyester, polycarbonate, polyvinyl chloride, polyethersulfone, polyacrylate, hydrogel, polysulfone, polyetheretherketone, thermoplastic isomers, thermoset elastomers, poly-p-xylylene, and fluoropolymers. Blends of polymers include, but are not limited to: polystyrene and polyphenylene oxide, polyethylene terephthalate and polybutylene terephthalate, and PMMA and polyvinylidene fluoride. Medical grade plastics include compositions including fillers, reinforcement and composites (such as glass), mineral powders, or carbon. Medical grade plastics include compositions described above and have been treated with biocidal or biofilm resistant materials as either coatings or as permeated within the polymer itself (i.e., halogens, plasmas, etc.).

DRAWINGS

Now referring to the drawings, FIG. 1 is a lateral view of the ILC with detachable tubing carriage. The catheter 100 is inserted into a patient's vessel. The most anterior end has openings 110, 111, 112. These openings correspond to lumens 103, 104, 105 which are connected to the catheter 100 at the junction hub 101. Each opening 110, 111, 112 corresponds with its own lumen 103, 104, 105. The junction hub 101 is configured to connect the catheter 100 with a set of lumens, and as shown, three lumens 103, 104, 105 are shown. In other embodiments, fewer or more lumens may be provided (i.e., one, two, or up to ten lumens may be provided). The openings always correspond to the number of lumens provided in any configuration.

The junction hub 101 provides connection between the catheter 100 and lumen(s) 103, 104, 105. The junction hub 101 may also have at least one suture hook 102. As shown, two suture hooks 102 may be provided. The suture hooks 102 provide an anchor to the patient by sutures to the patient's skin. As is well known to those in the art, the junction hub 101 may be sutured to the patient through the use of the suture hooks 102. At the posterior end of the junction hub 101, lumens 103, 104, 105 protrude therefrom, the lumens being received by a base 106. The base 106 is configured to receive the lumens 103, 104, 105. In some embodiments, the base 106 may receive between one and ten lumens. In this embodiment, as shown, three lumens 103, 104, 105 come from the junction hub 101 to the base 106.

The lumens 103, 104, 105 extend from the posterior end of the junction hub 101 through the base 106. The base 106 is adapted to receive a screw cap 107. The screw cap 107 terminates at its posterior end in a tubing carriage 108. The tubing carriage 108, shown in this embodiment, is used when desired but is not necessary in other embodiments. The tubing carriage 108 houses connections to the extension lumens 113, 114, 115. The extension lumens connect to and correspond with their associate lumens 103, 104, 105. The extension lumens 113, 114, 115 terminate at their posterior end in a lumen stop 109. Lumen stops 109 are well known in the art, and are a means of terminating a lumen with closure.

Figure 2:
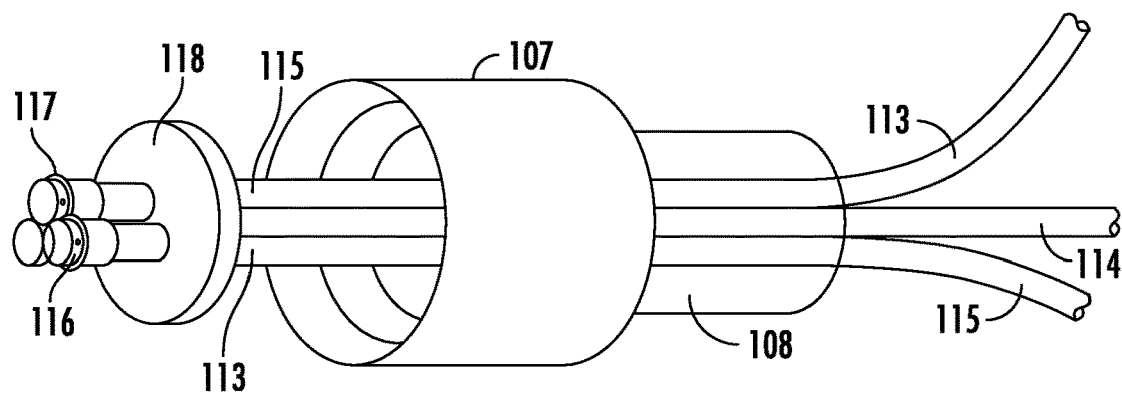
FIG. 2 is an illustration of the ILC with detachable tubing carriage, as in one embodiment.

FIG. 2 is an illustration of the ILC cap with detachable tubing carriage illustrating positioning of the extension lumens. The most anterior portion of this illustration shows the lumen junction 117 that connects the lumens (103, 104, 105 in FIG. 1) with the lumen extensions 113, 114, 115. The lumen junction 117 includes male inserts 116 that serve as a connection point by inserting into the posterior end of the lumens 103, 104, 105. The anterior portion of the extension lumens 113, 114, 115 are fitted with the male inserts 116 and the lumen junction 117 and then secured within the screw cap 107 by a capped end with a penetrable layer 118. The screw cap 107 is connected posteriorly to the tubing carriage 108. In one embodiment, the diameter of the capped end with a penetrable layer 118 is of approximately 2.5 cm. In some embodiments, the capped end with a penetrable layer is constructed of a sterile medical grade plastic. The screw cap 107, in one embodiment, is approximately 3 cm in diameter and is constructed of medical grade plastics, thermoset polymers, antibacterial coated, or permeated plastics and the like. In other embodiments, the tubing carriage 108 is approximately 5-6 cm in diameter and may be constructed of any number of durable impermeable plastics, such as medical grade plastics.

FIG. 3 is a close up view of an embodiment of the screw cap 107 of the ILC. This illustration further depicts the male inserts 116 and the lumen junction 117 that connects the extension lumens 113, 114, 115 to the lumens (not shown in this illustration). The extension lumens are secured in placement by the capped end with penetrable layer 118 and fit within the screw cap 107. Note, thought FIG. 3 depicts a configuration using three extension lumens, it is contemplated that between one and ten lumen extensions may be housed within the capped end with penetrable layer 118 and the screw cap 107. The anterior end of the screw cap 107 also shows threading 139 that is adapted to receive and connect with the flanges and threading on the base 106 (see FIG. 8).

FIG. 4 depicts a male insert connecting to an extension lumen. The male insert 116 has at least one protrusion serving to anchor the male insert 116 within the female insert 119 (FIG. 5). The male insert 116 has a lumen junction 117 which is a raised portion adapted to meet with and be flushed with the female insert 119 (FIG. 5) when connected. The male insert 116 has a posterior end that fits within the extension lumen 113, 114, or 115. In some embodiments, the interior diameter of the male insert 116 is approximately 5 mm. In those embodiments, the height of the flange from the male insert 116 is approximately 1 mm. The outer diameter of the lumen junction 117 is approximately 10 mm and the width of the lumen junction 117 is approximately 8 mm. The length of the male insert 116 is approximately 12 mm, wherein 5 mm extends within the female insert 119, and 5 mm extends within the extension lumen 113, 114, 115. In most embodiments, the male insert 116 and lumen junction 117 are constructed in one piece and are made of impermeable plastics such as medical grade plastics.

FIG. 5 shows the connection point between the lumens 103, 104, 105 and the extension lumens 113, 114, 115. The female insert 119 extends from an anterior end that is anchored within the lumen to a posterior end that may be received by a male insert 116 (FIG. 4). The female insert 119, in one embodiment, is approximately 5 mm in diameter at its anterior end and approximately 5 mm at its posterior end. The female insert 119 may be constructed in one piece and made of impermeable plastics, such as medical grade plastics.

Figure 6:
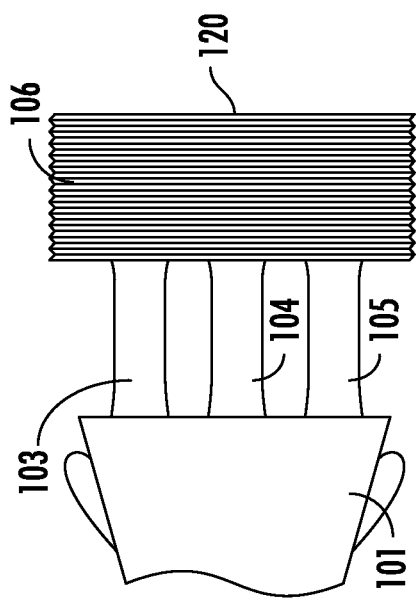
FIG. 6 is a lateral view of the base of the ILC, as in one embodiment.

FIG. 6 is a lateral view of the base of the ILC, as in one circular embodiment. The junction hub 101 is shown with the lumens 103, 104, 105 extending from the posterior edge. As has been stated, any number of lumens between one and ten may extend from the junction hub 101. The lumens 103, 104, 105 extend to the base 106 which houses and secures the lumens 103, 104, 105. In some embodiments, the base is circular in shape and is approximately 5 cm in diameter. The base 106, as in other elements of the ILC, may be made of impermeable, medically advantageous plastics and synthetics, such as medical grade plastics (see above). The base 106 has a posterior end that has threading 120 adapted to receive the screw cap 107 (see FIG. 2 and FIG. 3).

Figure 7:
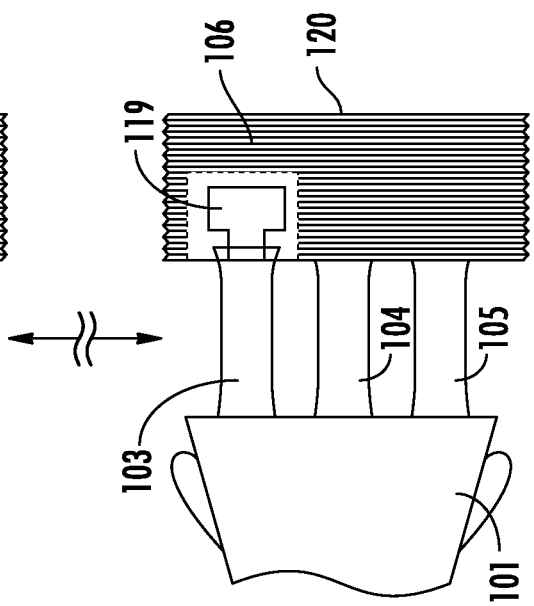
FIG. 7 is a cut-away lateral view of the base of the ILC, as in one embodiment.

FIG. 7, similar to FIG. 6, shows a lateral view of the base of the ILC, as in one circular embodiment, while showing a cut-away of the lumen 103 within the base 106. Each lumen, no matter the number in any embodiment, terminates within the base 106. The lumen 103, as depicted in FIG. 6, terminates within the base 106 with the female insert 119 described in detail by FIG. 5. The threading 120 is also shown in this illustration, as described further in FIG. 6.

Figure 8:
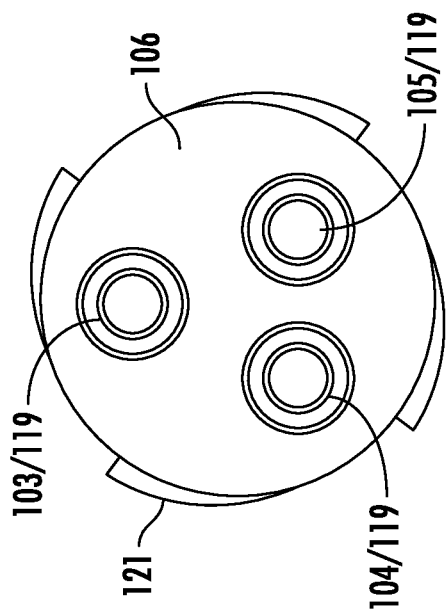
FIG. 8 is a posterior view of the base of the ILC, as in one embodiment.

FIG. 8 is a posterior view of the base of the ILC, as in one circular embodiment. This posterior view shows the lumens 103, 104, 105 within the base 106 and fitted with the female insert 119. A plurality of flanges 121 exist on the base 106. Whereas FIG. 8 depicts four flanges 121 on the outside of the base 106, it is contemplated and well within the knowledge of someone of skill in the art to provide anywhere between three and twenty flanges to provide a secure fitting between the base 106 and the screw cap 107.

Figure 9:
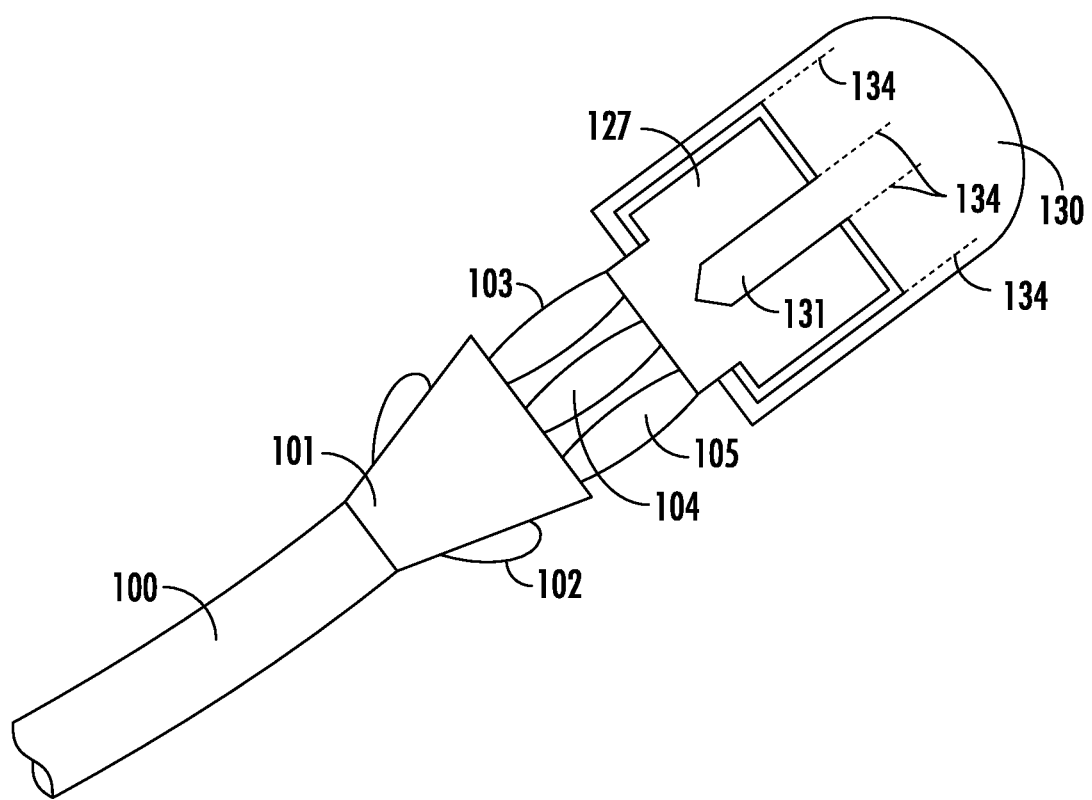
FIG. 9 is a view of the flat embodiment of the ILC.

FIG. 9 is an alternate configuration of the ILC. This configuration is substantially flat in nature, thus providing further advantages to patients in terms of comfort and profile (being lower in profile). As in the first embodiment described in FIGS. 1-8, the catheter 100 is placed within the vessel of a patient. The openings 110, 111, 112, as shown in FIG. 1, will be present in the most anterior end of the catheter 100 of the embodiment of FIG. 9. Those openings correspond to lumens 103, 104, 105 which are connected to the catheter 100 at the junction hub 101. Each opening 110, 111, 112 corresponds with its own lumen 103, 104, 105. The junction hub 101 is configured to connect the catheter 100 with a set of lumens, in FIG. 1, three lumens 103, 104, 105. In other embodiments, fewer or more lumens may be provided (i.e., one, two, or up to ten lumens may be provided). The openings always correspond to the number of lumens provided in any configuration.

Still in FIG. 9, the junction hub 101 provides connection between the catheter 100 and lumen(s) 103, 104, 105. The junction hub 101 may also have at least one suture hook 102. As shown in FIG. 1, two suture hooks 102 may be provided. The suture hooks 102 provide an anchor to the patient. As is well known to those in the art, the junction hub 101 may be sutured to the patient through the use of the suture hooks 102. At the posterior end of the junction hub 101, lumens 103, 104, 105 protrude therefrom, the lumens being received by a base 127. The base 127 is configured to receive the lumens 103, 104, 105. In some embodiments, the base 127 may receive between one and ten lumens. In this embodiment, FIG. 1 shows three lumens 103, 104, 105 come from the junction hub 101 to the base 127. Unseen in this illustration is a lower flange 128 (see FIG. 13) that will connect with the lower hook like extension in the base (not shown but mirroring 131 in FIG. 11).

The base 127 is configured to receive a cap 130. The cap 130, in this embodiment, is tamper evident and tamper resistant. The cap 130 has multiple points of contact, including an upper hook like extension (and lower) 131 and multiple perforated clips 134 for break-away use. A lower hook like extension 131 is not shown but mirrors the upper hook like extension both in shape and position. In this embodiment, the posterior position of the cap 130 is impermeable and does not house extension lumens, as in the previous embodiment. However, the presence of a similar tubing carriage is contemplated and may be used in this embodiment with adjustments to the cap, including an opening to receive the tubing carriage.

Figure 10:
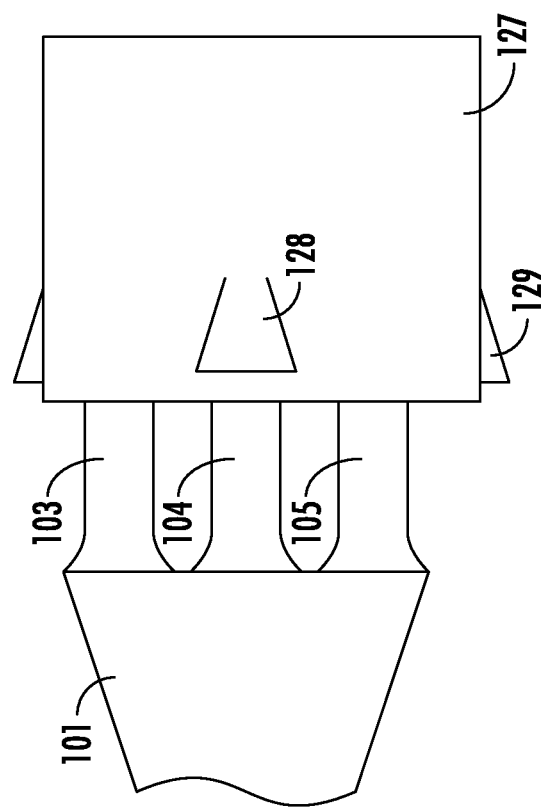
FIG. 10 is a lateral view of the base portion of the ILC, as in one embodiment.

FIG. 10 illustrates a close up lateral view of the flat base 127, as in one embodiment of the ILC. The anterior end of the base 127 receives the lumens 103, 104, 105. In some embodiments, the base 127 may receive between one and ten lumens. The base 127 is equipped with a plurality of flanges 128, 129. The lateral flanges 129 will connect with the cap 130 and anchor the ILC such that it is tamper resistant and tamper evident. There is also an upper flange 128 further anchoring the cap 130 to the base 127 in this embodiment of the ILC. In some embodiments, the base 127 is approximately 5 cm wide (lateral), 2 cm in length (anterior/posterior), and 10 mm thick. The lateral flanges 129 protrude 2 mm from the base 127 at their highest point and are generally shaped as an inclined rhombus with the posterior portion flushed with the base 127. The lateral flanges 129 protrude outward to a highest point located most anterior to the base 127. The upper and lower flange 128 may be trapezoidal in shape and similarly are flushed with the base 127 at its posterior end and extend outward from the base 127 to a measurement of approximately 2 mm at its anterior end. Unseen in this illustration is a lower flange 128 (see FIG. 13) that will connect with the lower hook like extension in the base (not shown but mirroring 131 in FIG. 11). As is well known in the art, other shapes that allow for the secure application of the cap are contemplated for use in the ILC.

Figure 11:
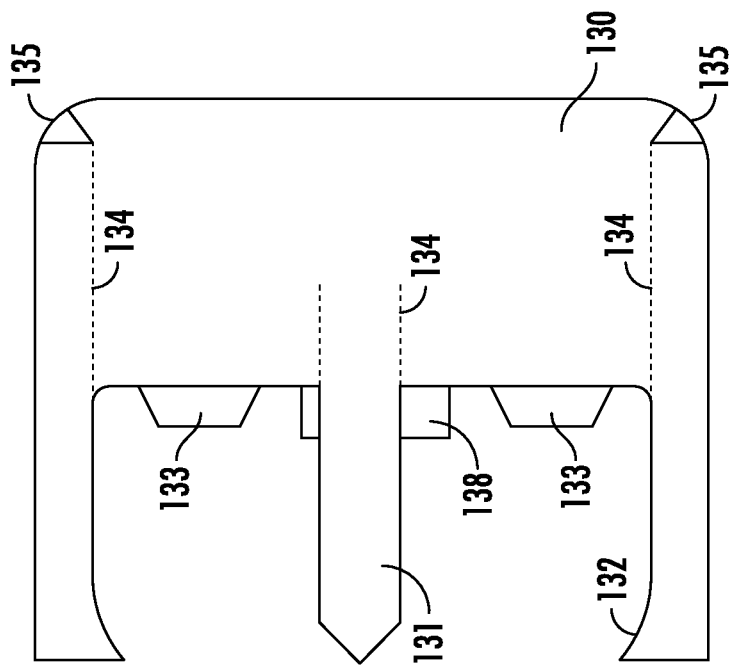
FIG. 11 is a lateral view of the cap portion of the ILC, as in one embodiment.

FIG. 11 depicts a lateral view of the cap 130 of the ILC in a flat embodiment. The cap 130 has two lateral (side) extensions terminating in a hook like extensions 132 and capable of connecting and latching to the flanges 128 and 129 of the base 127 (see FIG. 10). The cap 130 also has an upper hook like extension 131 capable of receiving and locking to the upper flange 128 on the base 127, as well as a lower hook like extension not depicted but mirroring the upper hook like extension 131. Male inserts 133 protrude from the middle portion of the cap 130 and fit within the lumens 103, 104, 105 housed within the base 127. A plurality of male inserts 133 may be used and should be of the same number as the number of lumens present (as stated, anywhere between one and ten). The cap 130 also has two notches 135 that may serve as insertion points for a clamp removal device (not shown). On the same plane as the two lateral hook-like extensions 132 and upper and lower hook-like extensions 131 are perforated edges 134. These perforated edges 134 allow for the cap 130 to be excised from the base 127 through a break-away of the perforated edges 132. In this embodiment, the lateral perforated edges extend from the hook-like extension 132 posterior to the edge of the cap 130 near the notches 135. The medial and upper and lower hook like extensions 131 have perforated edges posterior about three quarters of the length of the entire cap 130 (as measured from the lateral hook like extensions 132 to the most posterior edge of the cap).

In some embodiments, the length of the cap 130 from the most anterior edge of the lateral hook-like extension 132 to the posterior edge is approximately 1 cm. The approximate distance between the anterior edge of the lateral hook-like extension 132 to the medial edge where the male inserts 133 are housed is 4 mm. The male inserts 133 protrude approximately 1 mm from the medial edge. While the shape of the medial and upper hook and lower like extensions 131 are shown terminating in a point, it is well known to those skilled in the art that the shape may be anything adapted to receive and connect with the upper flange 128 on the base 127 (i.e. circular, rectangular, trapezoidal, rhomboid and the like). A third center lumen cap 138 is provided.

Figure 12:
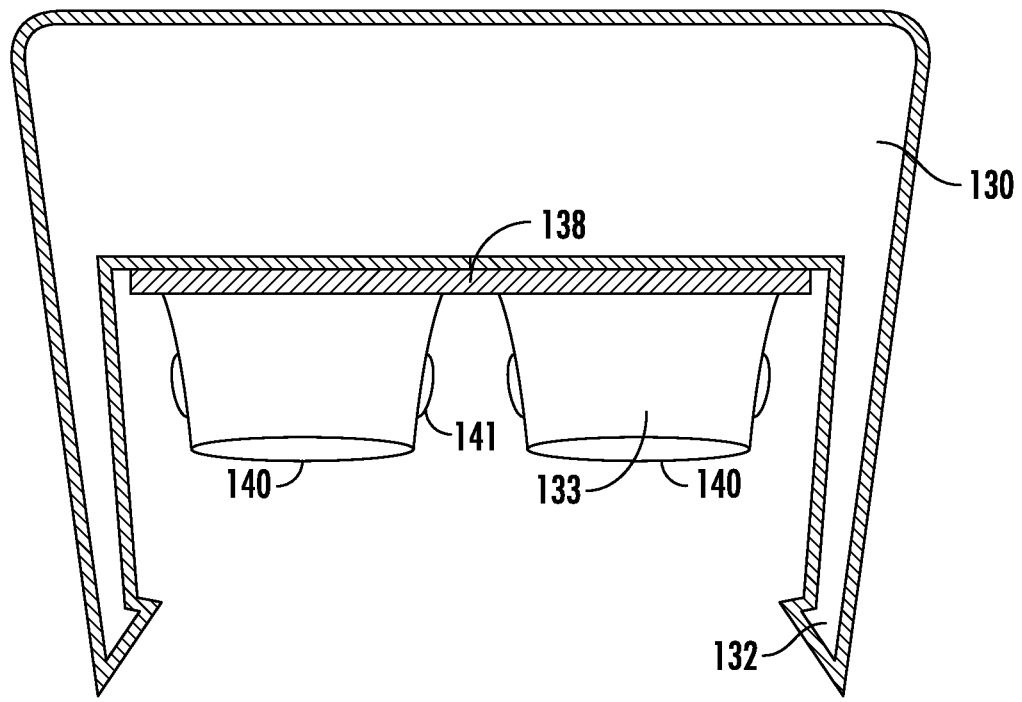
FIG. 12 is an alternate lateral view of the cap portion of the ILC, as in one embodiment.

FIG. 12 is an alternate lateral view of the cap portion, as in another embodiment of the ILC. In this embodiment, the lateral hook-like extensions 132 protrude from the cap 130 and two male inserts 140 are shown. In this embodiment, two lumens would be present in the base for fitting with the cap 130. The male inserts 140 are shown with two lateral protrusions 141 which serve to further anchor the inserts 140 into the lumens. This configuration is illustrated in FIG. 4, and may be employed in any male insert in any of the embodiments. Also note, in this embodiment, no medial and upper hook like extension 131 (see FIG. 11) is present. An edge 138 provides further contact and structural support to the cap 130 in this embodiment. Dimensions of this embodiment are similar to that depicted in FIG. 11. For example, the length of the cap 130 from the most anterior edge of the lateral hook-like extension 132 to the posterior edge is approximately 1 cm. Moreover, the approximate distance between the anterior edge of the lateral hook-like extension 132 to the medial edge where the male inserts 133 are housed is 5 mm. Similarly, the male inserts 133 protrude approximately 5 mm from the medial edge.

Figure 13:
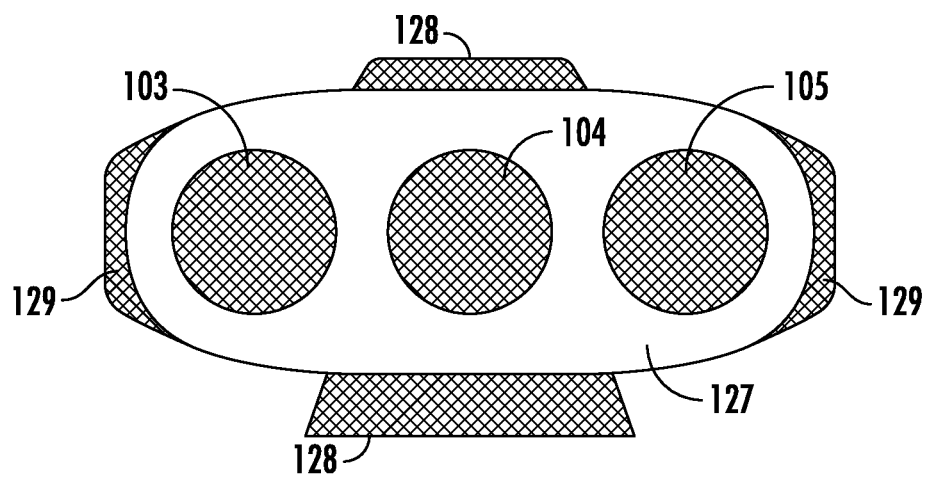
FIG. 13 is another view of the base portion of the ILC, as in one embodiment.

FIG. 13 is a posterior view of the base portion of the ILC in a flat embodiment. In this view, positioning of the lumens 103, 104, 105 is shown within the base 127. The lateral flanges 129 and upper and lower flanges 128 are shown protruding from the base 127 reaching their highest point near the anterior edge of the base 127. As shown in this embodiment, the flange 128, 129 shape is rectangular in nature, and may have either sharp or curved edges. As described, the flanges 128, 129 may be rhomboid in shape and serve to secure the cap 130 to the base 127.

Figure 14:
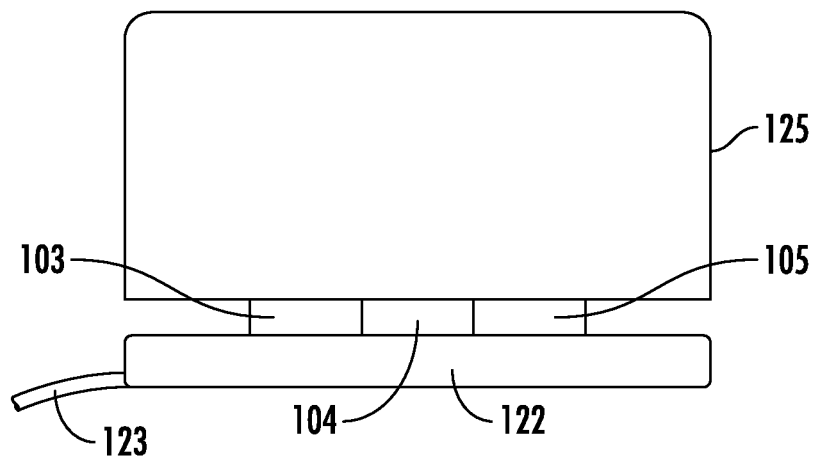
FIG. 14 is an alternate lateral view of the cap of the ILC, as in one embodiment.

FIG. 14 is a lateral view of the cap of yet another embodiment of the ILC. In this embodiment, the cap 125 has a break away twist cap attachment allowing for a twisting motion to loosen the cap 125. A pull tab 123 allows for access to pull away from the push insert base 122 that would house the lumens 103, 104, 105. The cap 125 would house male inserts for the capping of the lumens in this configuration. In this embodiment, the cap 125 is substantially circular in shape, wherein the diameter of the cap is approximately 5 cm and the length is approximately 3 cm. The cap 125 is constructed of medical grade plastics or synthetics that harbor microbially resistant elements. The insert base 122 is approximately 1 cm wide and 5 cm in length and being constructed of the same materials as the cap 125.

Figure 15:
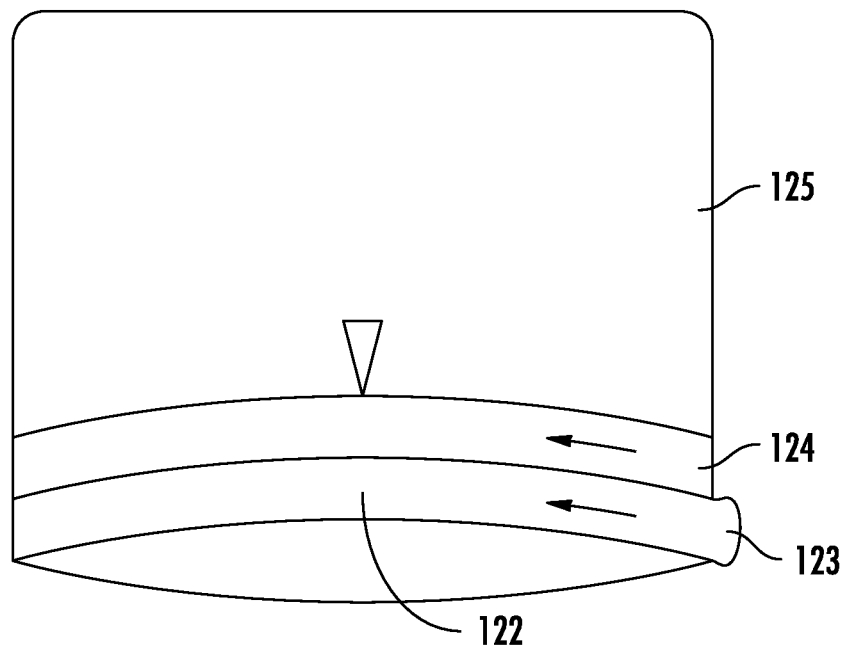
FIG. 15 is a view of yet another lateral view of the cap of the ILC, as in one embodiment.

FIG. 15 is yet another embodiment of the cap of the ILC as viewed laterally. In this embodiment, the cap 125 has a removable portion 124 at its anterior end which may be accessed by pulling a protruding tab 123 that will then be stripped from the main body of the cap 125 through two perimeters of the cap 125. The cap 125 is adaptable to receive a push insert base 122 (see FIG. 14) that houses the lumen(s). Not shown are the male inserts within the cap 125 for filling and capping the lumen(s) in this embodiment. In this embodiment, the cap 125 is substantially circular in shape, wherein diameter of the cap is approximately 5 cm. The cap 125 is constructed of medical grade plastics or synthetics that harbor microbially resistant elements. The tab 123 and removable portion 124 are approximately 10 mm in length.

Figure 16:
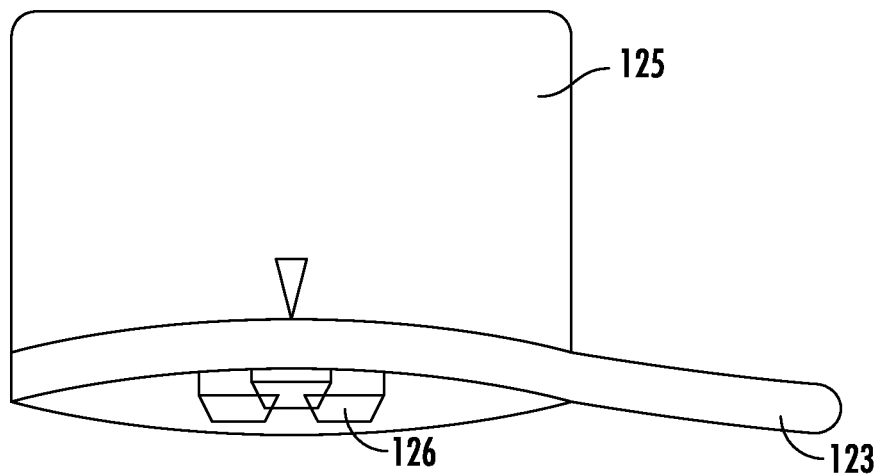
FIG. 16 is a lateral view of the cap portion of the ILC, as in one embodiment.

FIG. 16 shows the embodiment as in FIG. 15, wherein the tab 123 has been pulled and a portion of the anterior end of the cap 125 has been removed, thus revealing the male inserts 126 contained therein. While this illustration depicts the inserts 126 in a conical and sloped type shape which can be used in any of the embodiments described herein, the inserts 126 may be adjacent and lateral to one another. Whatever configuration is chosen for the male inserts 126, the cap 125 will be mirrored by the corresponding push insert base 122.

Figure 17:
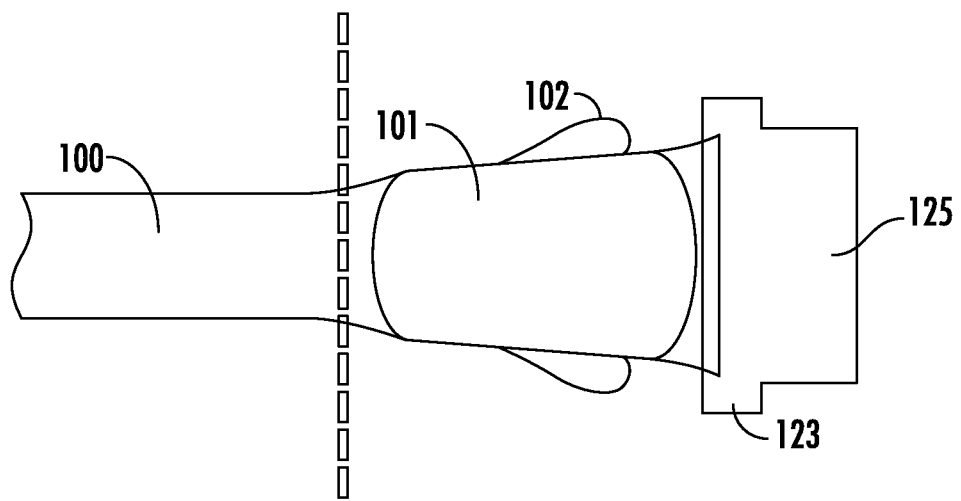
FIG. 17 is a view of yet another alternate embodiment of the ILC.

FIG. 17 is an alternate embodiment of the ILC. In this embodiment, the catheter 100 is within the vessel of the patient and the dashed line represents the insertion point into the skin. The junction hub 101 is shown with two lateral suture hooks 102. The lumens are not visible and would be positioned by a push insert base (see FIG. 14) to be received by the cap 125 (having male inserts 126 to cap off the lumens). This embodiment shows the pull tab 123 removal system, where the tab may be pulled to expose the anterior end of the cap for removal by a medical caregiver.

Figure 18:
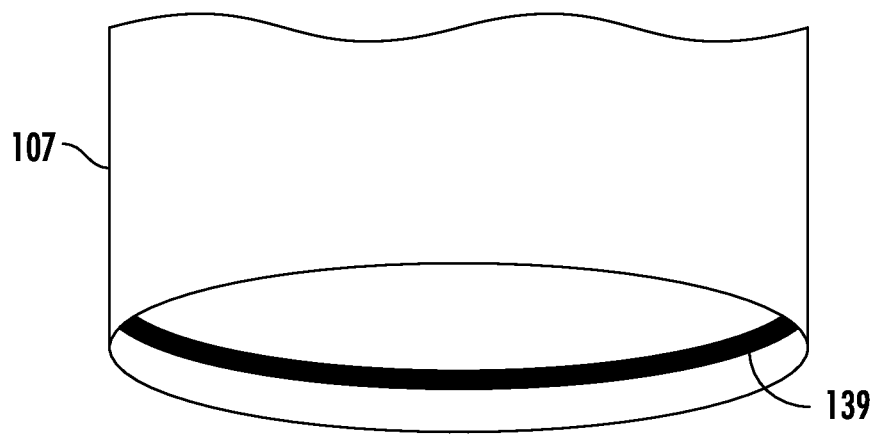
FIG. 18 is a view of the cap of the ILC, as in one embodiment.

FIG. 18 is a cap of a circular embodiment of the ILC. The cap 107 is circular and constructed of medical grade plastics. The interior of the cap has a recessed portion 139 capable of receiving threading located on the base (see FIG. 19). In one preferred embodiment, the diameter is approximately 5 cm. As will be understood by those skilled in the art, this embodiment will receive a base 106 (see FIG. 19) housing three lumens. As different numbers of lumens are used, the diameter may change (i.e., where ten lumens are contemplated the diameter will necessarily larger, by proportion).

Figure 19:
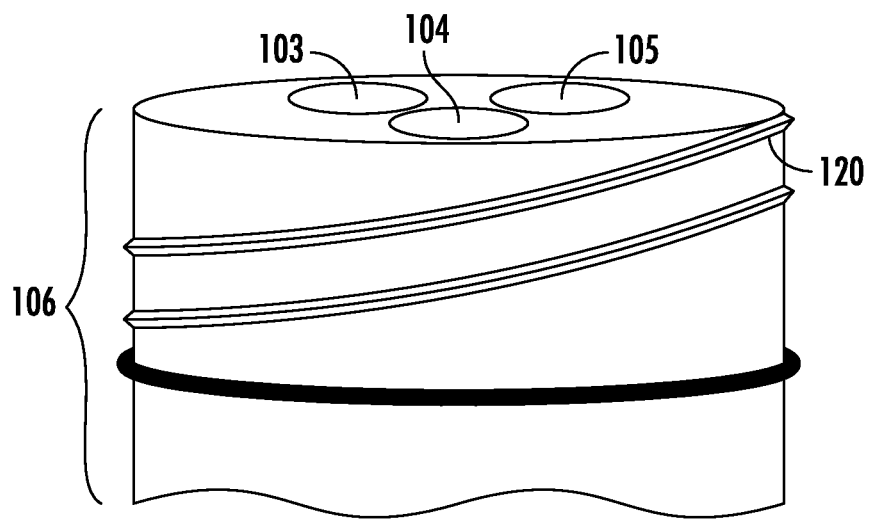
FIG. 19 is a lateral view of the base of the ILC, as in one embodiment.

As shown in FIG. 19, the base 106 houses the lumens 103, 104, and 105, and has threading 120 on the exterior and posterior end of the base 106. A ridge is shown delineating the threaded portion of the base 106 in this embodiment of the ILC. As has been stated, the number of lumens housed within the base 106 will vary in many embodiments and contain between one and ten lumens. The base 106 is constructed of medical grade plastics and is of similar diameter to the cap 107 thus creating a seamless piece when the base 106 is connected to the cap 107.

Figure 20:
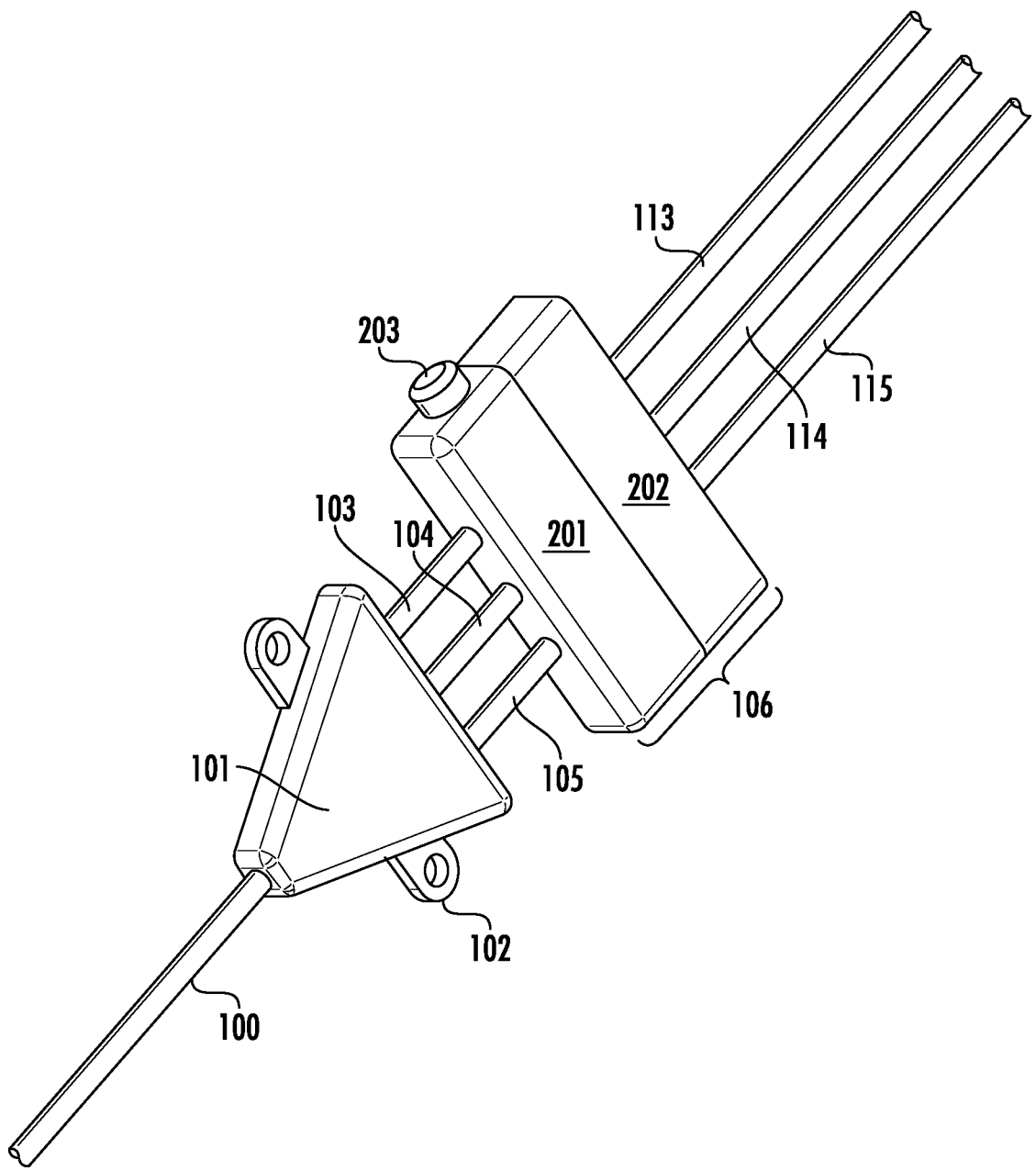
FIG. 20 is a perspective view of an embodiment of an ILC with quick release function.

As shown in FIG. 20, the base 106 is a two-piece 201 and 202 connection that is spring operated by pressing button 203. In other embodiments, fewer or more lumens may be provided as taught herein (i.e. one, two, or up to ten lumens or more may be provided). Lumen openings correspond, as in other embodiments shown herein.

Figure 21:
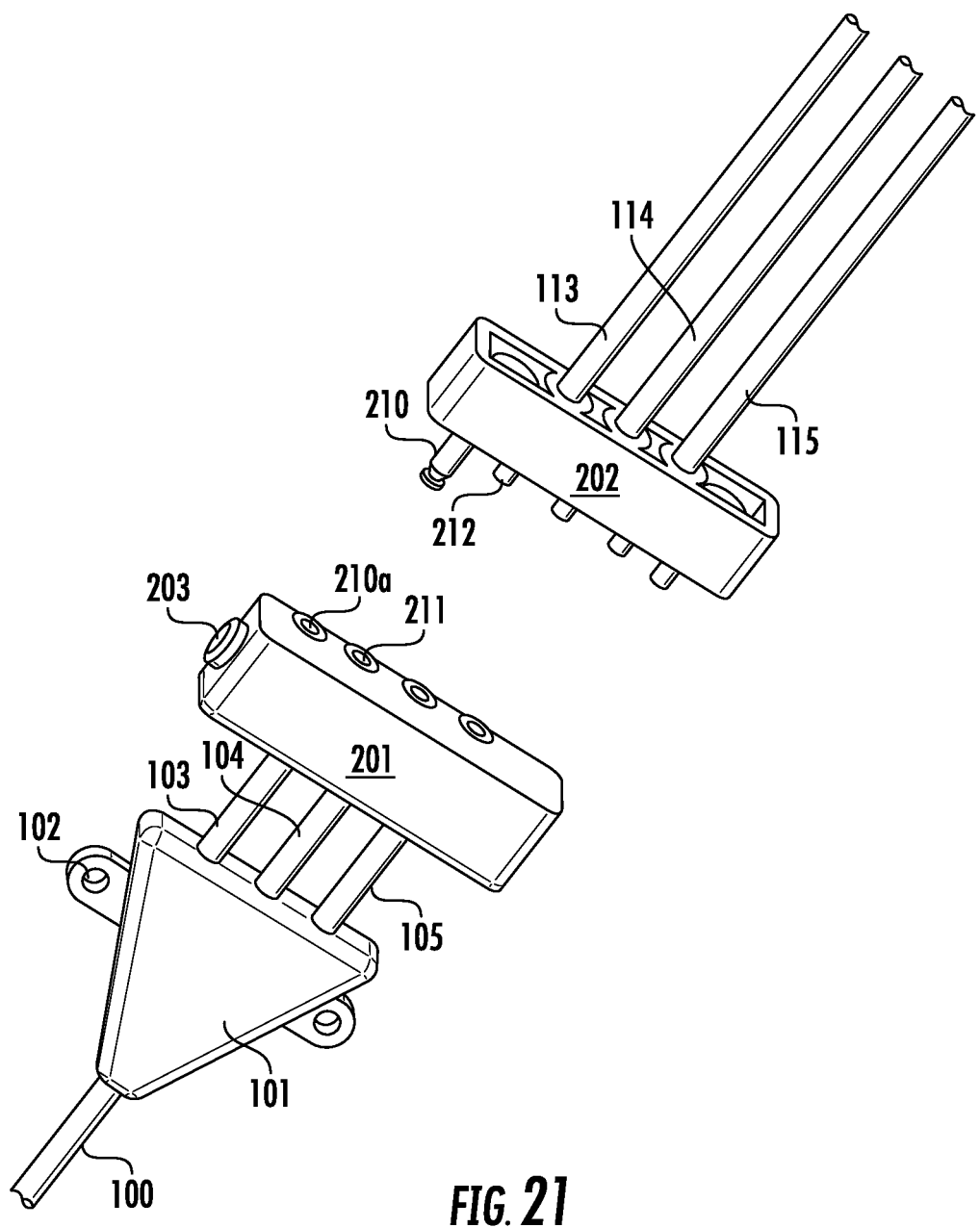
FIG. 21 is a perspective view of the device of FIG. 20 apart.
Figure 22:
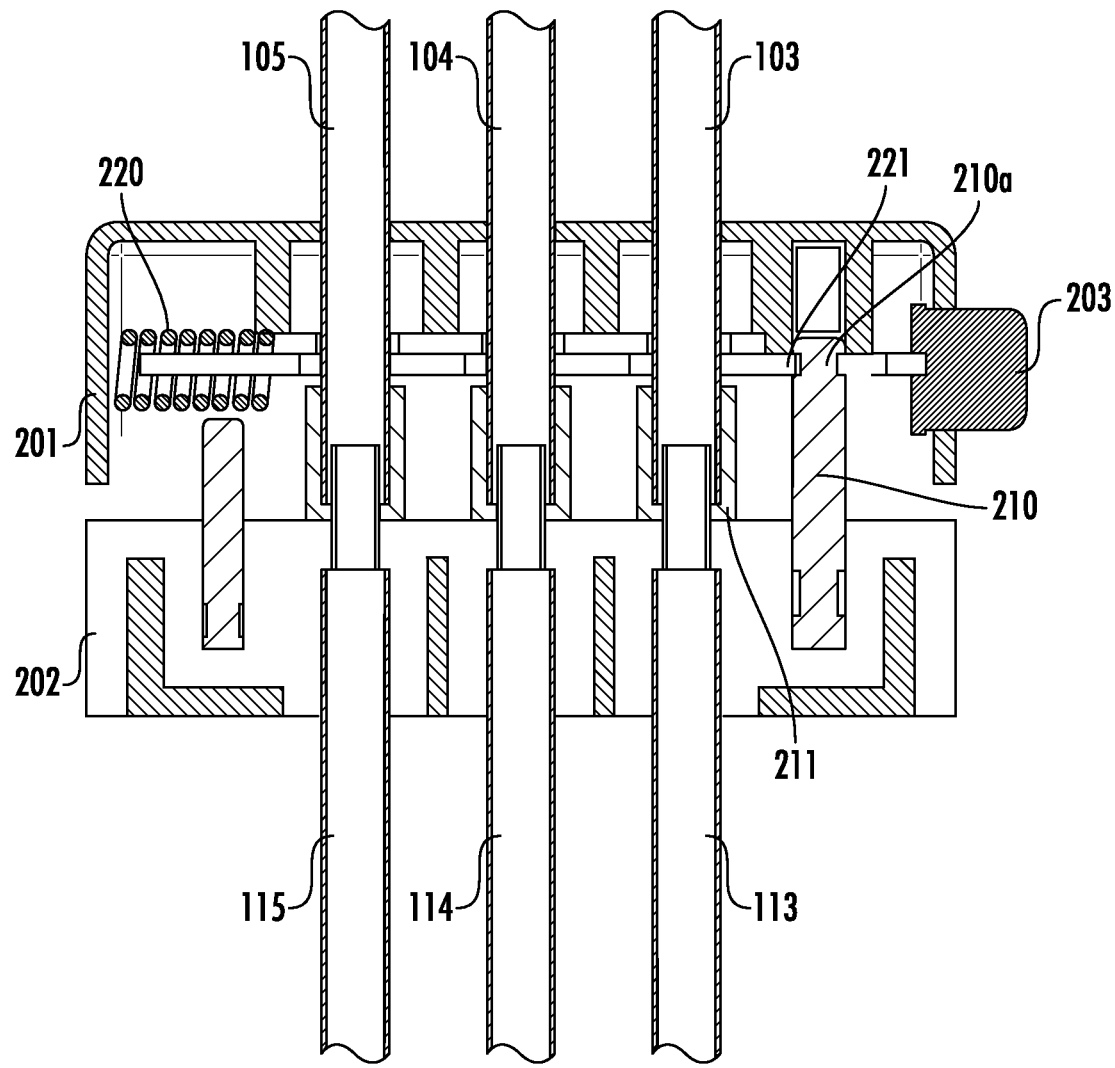
FIG. 22 is a cross section of the connector in FIG. 20.

FIG. 21 is a perspective view of the two piece base separated showing locking pin 210 which inserts into hole 210a and locks, as shown in FIG. 22. Lumen connections 212 fit into holes 211 for making a connection with extension lumens 113, 114, 115.

FIG. 22 is an x-ray view of the base in FIG. 20 in the locked position. In this view, one can see that spring 220 operates locking pin 221 which holds the locking pin 210 in place via hole 210a thus locking the two-piece pins 201 and 202 connection together unless button 203 is pressed compressing spring 220 and releasing locking pin 221 so that the base can be separated into two pieces.

Figure 23:
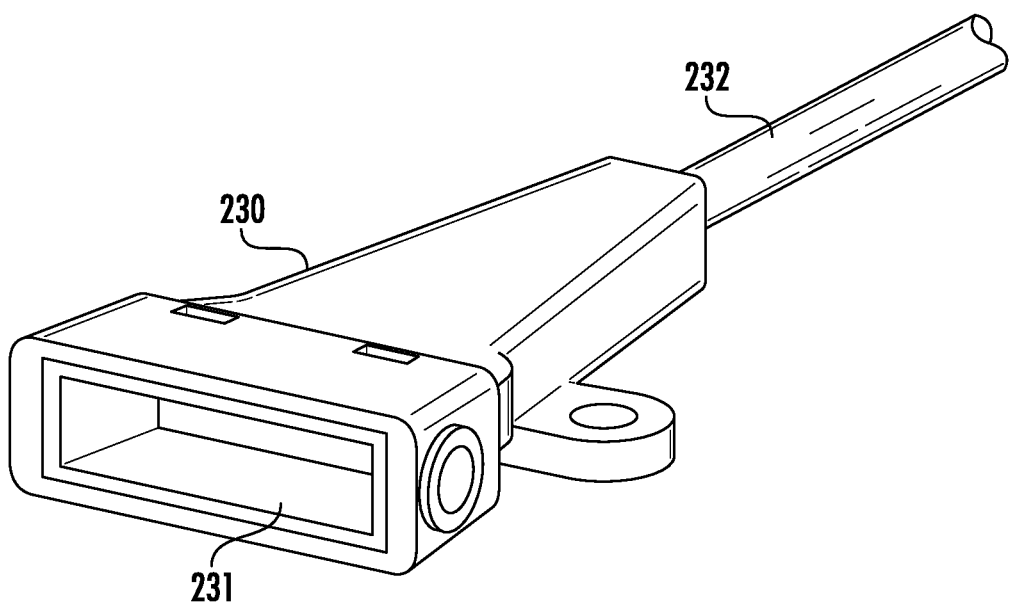
FIG. 23 is a perspective view of a safety plug inserted into a PICC base.

FIG. 23 is a perspective view of a safety plug 231 inserted into a PICC base 230 holding catheter tube 232.

Figure 24:
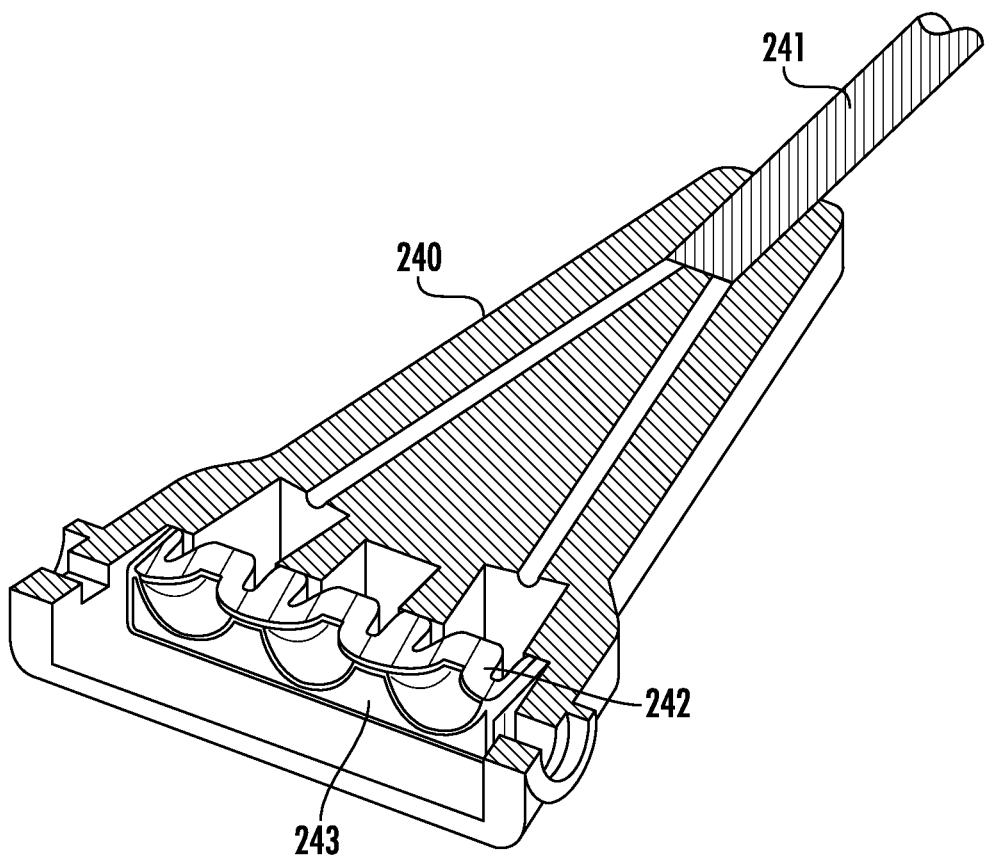
FIG. 24 is a cutaway perspective view of the base and catheter.

FIG. 24 is a cutaway perspective view of a base 240 and catheter 241. In this view, an adjustable valve 242 is shown having three valve positions. It is held in place via stainless steel retainer 243. The valves allow for opening and closing each valve.

Figure 25:
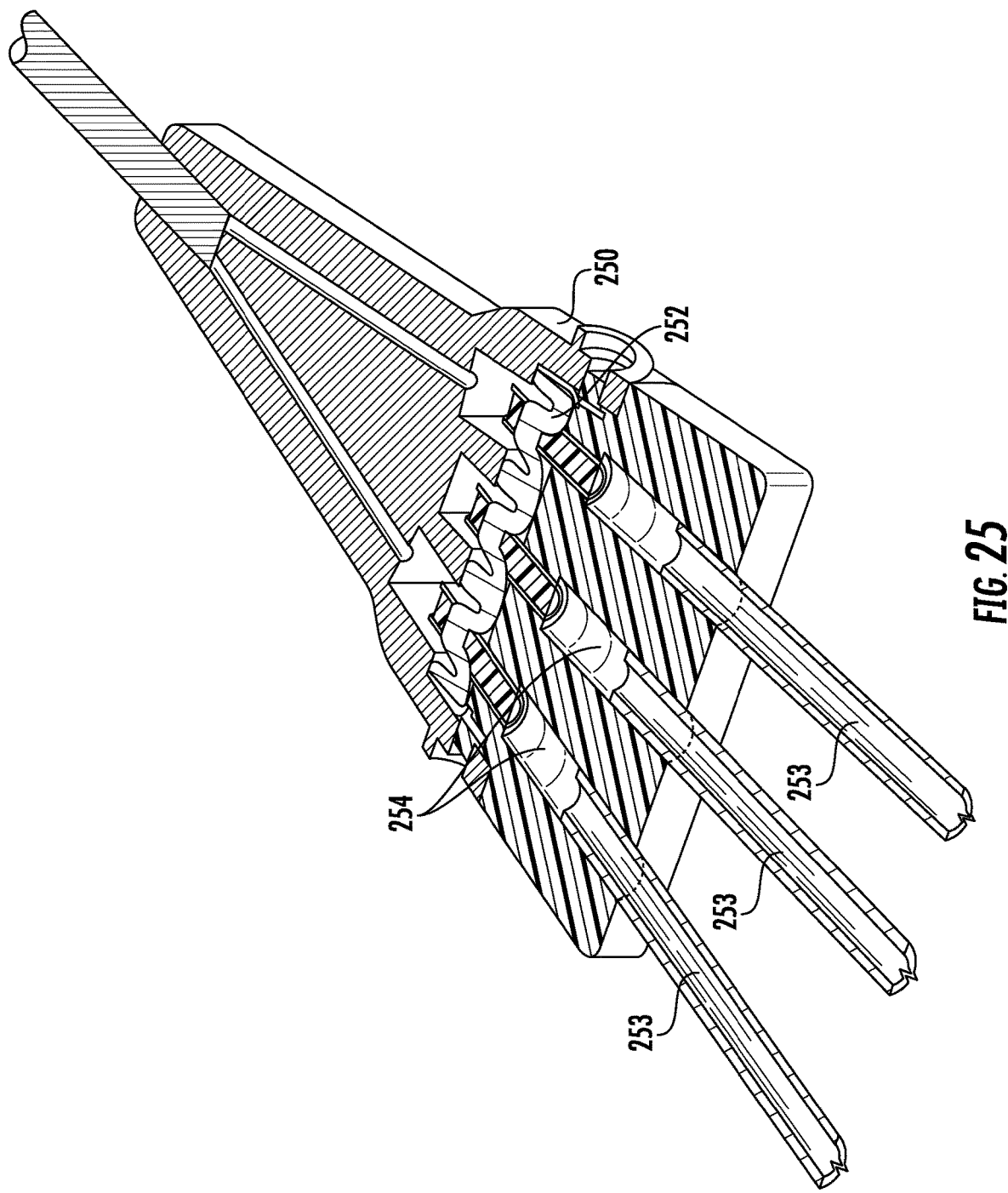
FIG. 25 is a cutaway perspective of the base.

FIG. 25 is a cutaway perspective view of the base. In this view, base 250 has adjustable valve 252 to open and close anything coming from each of tubes 253. A metal tube 254 connects tubing 253 to the adjustable valve 252.

While the compositions and methods of this disclosure have been described in terms of particular embodiments, it will be apparent to those of skill in the art that variations may be applied to the structures and/or methods and in the steps or in the sequence of steps of the method described herein without departing from the concept, spirit, and scope of the disclosure. All such similar substitutes and modifications apparent to those skilled in the art are deemed to be within the spirit, scope, and concept of the disclosure as defined by the appended claims. It will be understood that particular embodiments described herein are shown by way of illustration and not as limitations of the disclosure.

The principal features of this disclosure can be employed in various embodiments without departing from the scope of the disclosure. Those skilled in the art will recognize, or be able to ascertain using no more than routine study, numerous equivalents to the specific structures described herein. Such equivalents are considered to be within the scope of this disclosure and are covered by the claims. All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

What is claimed is:

1. An interchangeable lockable catheter (ILC) for use with a subject comprising:
   a) a single central catheter for peripheral insertion having a proximal end for insertion into a vessel of the subject and a distal end in communication with a single junction hub;
   b) wherein the single junction hub is connected to the distal end of the single central catheter, and the single junction hub has a plurality of lumens connected to the distal end of the central catheter;
   c) a two piece base spaced-apart from the single junction hub and being fluidly upstream of the single junction hub, the two piece base having a male piece and a female piece, wherein the plurality of lumens of the single junction hub terminate in the female piece of the base in spaced relationship to the junction hub, wherein the female piece connects multiple lumens of the female base to the multiple lumens of the male piece and connects the female piece lumens to each of lumens terminating in the male piece, wherein the male and female pieces are held together by a single rigid locking pin extending from the male piece and inserted into a recess in the female piece and the single rigid locking pin is held in place by a single spring-loaded locking pin in the female piece, which is locked and unlocked via a push button in the side of the female piece, which disengages the spring-loaded locking pin from the rigid locking pin; and
   d) a connecting lumen between each lumen with the base and the lumens in the junction hub,
      wherein the rigid locking pin extends parallel with the plurality of lumens
      extending from the male piece,
      wherein the junction hub defines a flat surface with apertures on opposing ends therefor for suturing the junction hub to the patient.

2. The ILC for use with a subject according to claim 1 herein the female piece of the base is adapted to receive a cap.

3. The ILC for use with a subject according to claim 2 wherein the cap is designed to be tamper resistant.

4. The ILC for use with a subject according to claim 2 wherein the cap is fitted with an impenetrable layer.

5. The ILC for use with a subject according to claim 1 wherein there are three lumens in the hub connecting to the central catheter.

6. The ILC for use with a subject according to claim 1 wherein there are one or more sutures or securing devices for securing the device to the subject.

7. The ILC for use with a subject according to claim 1 wherein the base is substantially flat in nature.

* * * * *